United States Patent
Liu et al.

(10) Patent No.: US 8,126,694 B2
(45) Date of Patent: Feb. 28, 2012

(54) MODELING CONDUCTIVE PATTERNS USING AN EFFECTIVE MODEL

(75) Inventors: Zhuan Liu, Fremont, CA (US);
Jiangtao Hu, Sunnyvale, CA (US);
Yudong Hao, Fremont, CA (US)

(73) Assignee: Nanometrics Incorporated, Milpitas, CA (US)

( * ) Notice: Subject to any disclaimer, the term of this patent is extended or adjusted under 35 U.S.C. 154(b) by 561 days.

(21) Appl. No.: 12/114,700

(22) Filed: May 2, 2008

(65) Prior Publication Data

US 2009/0276198 A1    Nov. 5, 2009

(51) Int. Cl.
*G06F 17/50* (2006.01)
*G06F 17/00* (2006.01)
*G06G 7/62* (2006.01)

(52) U.S. Cl. .......................... 703/13; 716/50
(58) Field of Classification Search ............. 703/13; 716/50

See application file for complete search history.

(56) References Cited

U.S. PATENT DOCUMENTS

| | | | |
|---|---|---|---|
| 5,472,814 A * | 12/1995 | Lin | 430/5 |
| 5,963,329 A | 10/1999 | Conrad et al. | |
| 6,362,414 B1 * | 3/2002 | Fujisawa et al. | 136/256 |
| 6,483,580 B1 | 11/2002 | Xu et al. | |
| 6,485,872 B1 | 11/2002 | Rosenthal et al. | |
| 6,654,108 B2 | 11/2003 | Ravid et al. | |
| 6,720,568 B2 | 4/2004 | Finarov et al. | |
| 6,940,592 B2 | 9/2005 | Borden et al. | |
| 7,202,958 B1 * | 4/2007 | McGahan | 356/630 |
| 7,379,192 B2 * | 5/2008 | Bischoff et al. | 356/602 |
| 2003/0210408 A1 | 11/2003 | Jun et al. | |
| 2004/0080761 A1 | 4/2004 | Du-Nour et al. | |
| 2004/0109173 A1 * | 6/2004 | Finarov et al. | 356/625 |

OTHER PUBLICATIONS

Germer, Thomas A. "Modeling the effect of line profile variation on optical critical dimension metrology", 2007, Proceeding of SPIE, vol. 6518, 9 pages.*
Warren et al. "Sub-wavelength Diffractive Optics", Mar. 1998, Sandia Report, 32 pages.*
Chen et al., "Application of Spectroscopic Ellipsometry-based Scatterometry for Ultrathin Spacer Structure", www.kla-tencor.com/magazine, Summer 2004, 5 pgs.
Office Action mailed on Aug. 1, 2006, for U.S. Appl. No. 10/859,330, filed Jun. 1, 2004, by McGahan, 8 pgs.
Response to Office Action, mailed on Nov. 1, 2006, for U.S. Appl. No. 10/859,330, filed Jun. 1, 2004 by McGahan, 10 pgs.
Notice of Allowance mailed Dec. 28, 2006, for U.S. Appl. No. 10/859,330, filed Jun. 1, 2004, by McGahan, 4 pgs. International Search Report and Written Opinion mailed on Jun. 22, 2009 for PCT Application No. PCT/US2009/042413 filed on Apr. 30, 2009 by Nanometrics Incorporated, 11 pages.

* cited by examiner

*Primary Examiner* — Kamini S Shah
*Assistant Examiner* — Suzanne Lo
(74) *Attorney, Agent, or Firm* — Silicon Valley Patent Group LLP

(57) ABSTRACT

A model of a sample with a periodic or non-periodic pattern of conductive and transparent materials is produced based on the effect that the pattern has on TE polarized incident light. The model of the pattern may include a uniform film of the transparent material and an underlying uniform film of the conductive material. When the pattern has periodicity in two directions, the model may include a uniform film of the transparent material and an underlying portion that based on the physical characteristics of the periodic pattern in the TM polarization direction. When the sample includes an underlying periodic pattern that is orthogonal to the top periodic pattern, the sample may be modeled by modeling the physical characteristics of the top periodic pattern and the effect of the bottom periodic pattern. The model may be stored and used to determine a characteristic of the sample.

32 Claims, 11 Drawing Sheets

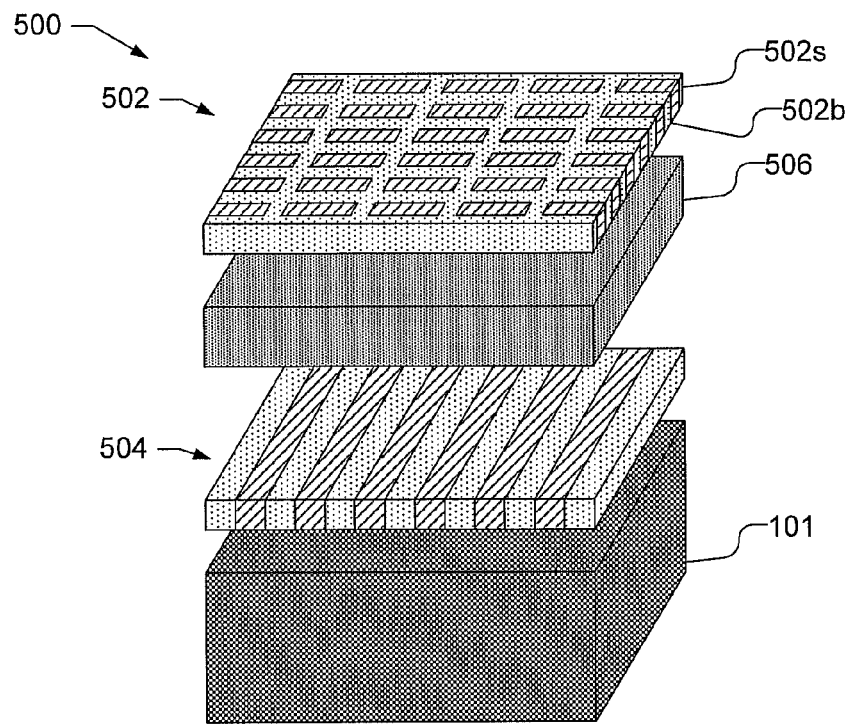
Fig. 13
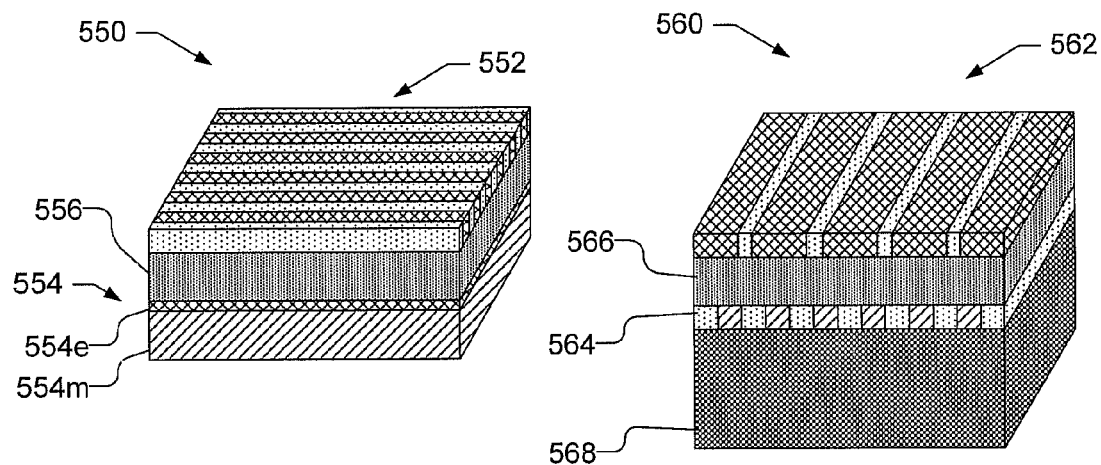
Fig. 15
Fig. 16

MODELING CONDUCTIVE PATTERNS USING AN EFFECTIVE MODEL

FIELD OF THE INVENTION

This invention relates, in general, to optical metrology and, in particular, to measuring a periodic pattern.

BACKGROUND

In multiple level interconnect structures in semiconductor processing, one of the major challenges is the dimensional control of the conductive interconnect features (the line width and height), which is critical to achieve necessary circuit performance of the device. To achieve optimum device performance, there is limited tolerance of the profile variation in interconnect structures. This dimensional control requirement demands metrology solutions to characterize the interconnect structures at all metal levels.

In one conventional metrology technique, a single measurement of the sample is made. The sample is modeled mathematically and the mathematically predicted data is compared to the measurement data. When a good fit occurs, the model is said to accurately describe the sample. The model may be repeatedly adjusted until the fit is considered to be within tolerance. In some systems, multiple varying models are generated and stored, along with their associated mathematically predicted data, in a library that is consulted during measurement of a sample.

Modeling techniques are particularly useful when the sample is a simple structure, such as uniform films. Unfortunately, when the sample is complicated, such as overlying orthogonally arranged periodic patterns, analytically modeling the sample can be difficult. For example, the test structure for a copper interconnect usually features stacked copper gratings with alternating orientations and different line pitches. Metrology solutions using scatterometry based techniques require 3D modeling for these structures, which are often impractical due to the structure complexity, large parameter space and serious parameter correlations.

Accordingly, what is needed is an improved optical metrology process that can be used to measure complicated sample structures.

SUMMARY

In accordance with one embodiment, a model of a sample with a periodic or non-periodic pattern of conductive material, such as a metal or metal alloy, and a transparent material, such as a dielectric, is produced based on the effect that the pattern has on the incident light that is TE polarized with respect to the pattern. The model of the pattern may include, e.g., a uniform film of an effective medium layer and an underlying uniform film of the conductive material. The effective medium layer may have the combined optical properties of the transparent material and the conductive material. When the pattern has periodicity in two directions, the model may include, e.g., a periodic pattern with a periodicity in a single direction. In one embodiment, the sample may have an underlying periodic pattern that is orthogonal to the top periodic pattern. Such a sample may be modeled based on the physical characteristics of the top periodic pattern and the effect of the bottom periodic pattern on the TE polarization. The model may be used to determine a characteristic of the sample.

BRIEF DESCRIPTION OF THE DRAWINGS

FIG. 13 illustrates an exploded perspective view of a sample with a two dimensional periodic pattern lying above another one dimensional periodic pattern.

FIG. 15 illustrates a perspective view of a model for the sample from FIG. 13 when incident light is TE polarized with respect to the top periodic layer.

FIG. 16 illustrates a perspective view of a model for the sample from FIG. 13 when incident light is TM polarized with respect to the top periodic layer.

DETAILED DESCRIPTION

Figure 1:
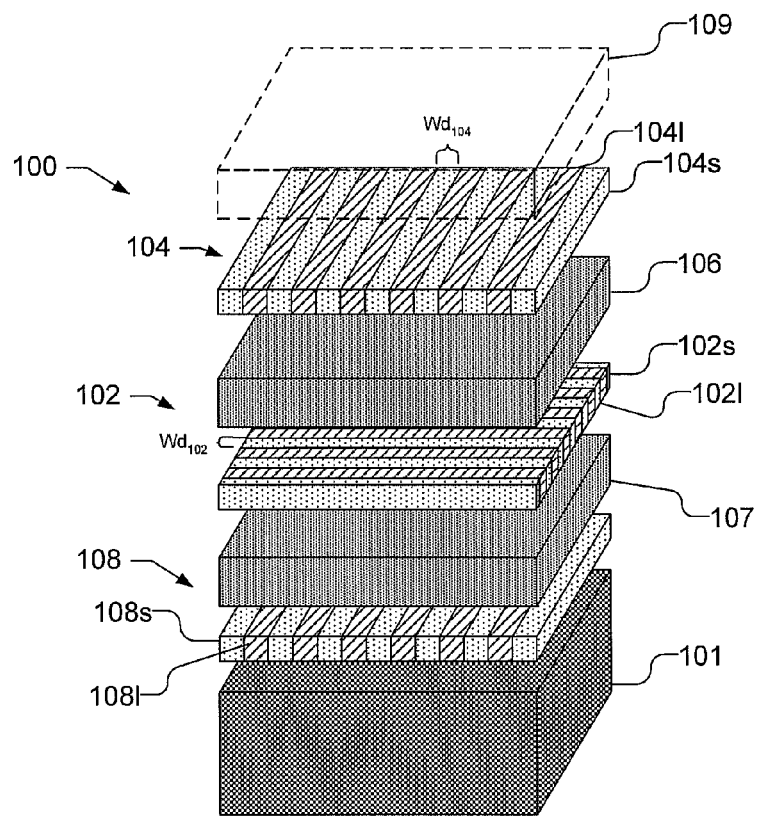
FIG. 1 illustrates an exploded perspective view of a sample that includes overlying periodic patterns, which are problematic to measure using conventional metrology techniques.

FIG. 1 illustrates an exploded perspective view of a sample 100 that is problematic to measure using conventional metrology techniques. The sample 100 includes a substrate 101 and two layers 102 and 104, which include overlying periodic patterns, such as line and spaces, at orthogonal orientations. It should be understood that the sample 100 may include additional layers that underlie layer 102, e.g., such as periodic pattern 108. Additionally, one or more transparent layers may be present over the top periodic pattern in layer 104, e.g., such as a layer 109 shown with broken lines.

The periodic patterns in layers 102 and 104, by way of example, may include lines 102*l* and 104*l* and spaces 102*s* and 104*s*. The lines 102*l* and 104*l* are formed from a conductive material, such as a metal or metal alloy and the spaces 102*s* and 104*s* are formed from at least partially transparent material, such as a dielectric. By way of example, the periodic patterns on layers 102 and 104 may be copper interconnect structures or alternatively test structures for copper interconnects. A dielectric layer 106, or a plurality of layers, may be disposed between the layers 102 and 104. A sample with a structure similar to that shown in FIG. 1 is difficult to measure due to the complexity of the structure which is further compounded by the orthogonal orientations of the patterns.

Figure 2A:
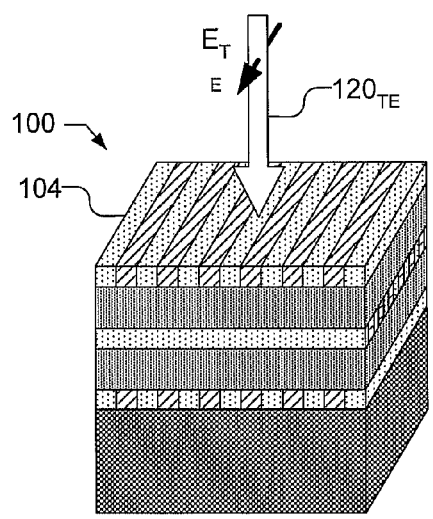
FIGS. 2A and 2B illustrate the sample being measured with TE and TM incident light, respectively.
Figure 2B:
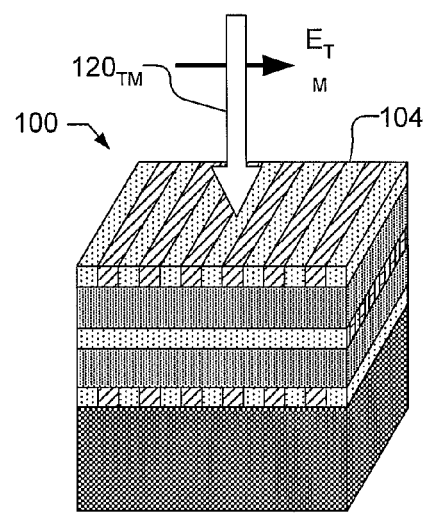

The sample 100, or a structure similar to sample 100, is measured using polarized light that has the electric field component either parallel or perpendicular to the periodic pattern on the top layer 104, which is sometimes respectively referred to as the Transverse Electric (TE) or Transverse Magnetic (TM) polarization states. Light with other polarization or unpolarized light can be decomposed into TE and TM polarizations. FIGS. 2A and 2B illustrate the sample 100 being measured with TE and TM incident light $120_{TE}$ and $120_{TM}$, respectively. In one embodiment, the incident light used to measure the sample is oriented normal to the surface of the sample 100.

When the width of the transparent material in the periodic pattern in the top layer 104, i.e., width $Wd_{104}$ in FIG. 1, is much smaller than the wavelength $\lambda$ of light that is to be used to measure the sample 100, e.g., less than $\frac{1}{2}\lambda$ or more particularly less than $\frac{1}{3}\lambda$, the top patterned layer 104 will appear as a solid surface when the incident light is TE polarized, i.e., the light will not penetrate through the top patterned layer 104 at a typical process window. This is the result of the requirement of electric field boundary matching in the TE polarization. Because surface charges do not induce electric field parallel to the surface, for the TE mode, the zero electric field intensity inside the conductive material requires the electric field between conductive material to be zero as well. This is different for the TM mode, where surface charges can induce electric field perpendicular to the conductive lines, allowing non-zero electric field between the conductive lines. Therefore, when the incident light is TM polarized with respect to the periodic pattern in the top layer 104, the light will pass through the periodic pattern and convey additional information about the periodic pattern, such as the pitch, width, height, and sidewall angle of the lines. Moreover, the TM polarized light will penetrate to the underlying patterned layer 102. However, because the periodic pattern in underlying layer 102 is oriented orthogonally with respect to the periodic pattern in the top layer 104, the incident light that penetrates the top patterned layer 104 will be TE polarized with respect to the periodic pattern in the underlying pattered layer 102. Accordingly, the underlying patterned layer 102 will appear as a solid surface if width of the transparent material in the periodic pattern in the underlying layer 102, i.e., width $Wd_{102}$ in FIG. 1 is much smaller than the wavelength $\lambda$ of the light, less than $\frac{1}{2}\lambda$ or more particularly less than $\frac{1}{3}\lambda$.

Figure 3A:
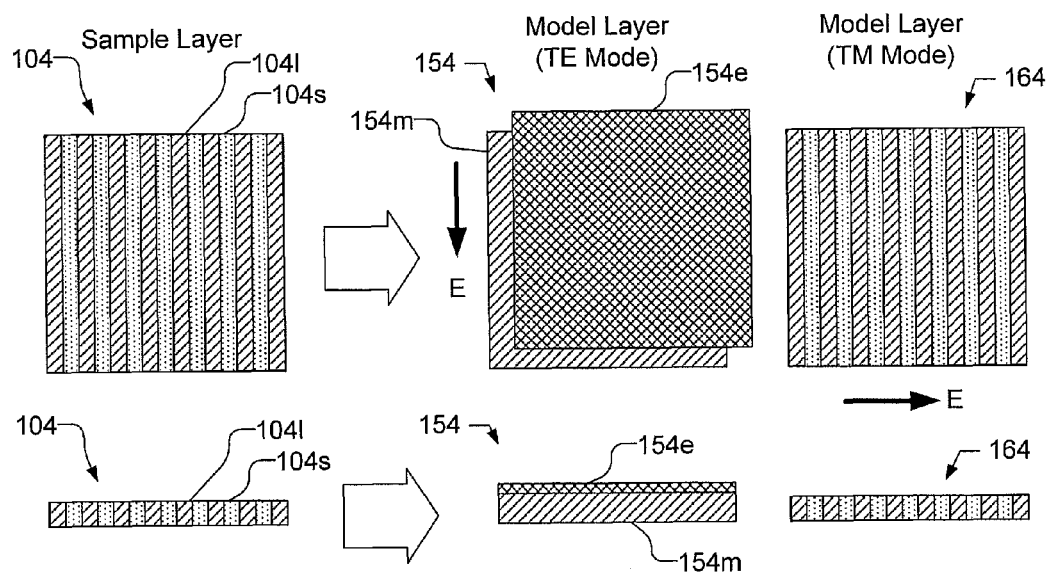
FIG. 3A illustrates a top plan view and a side view of the top patterned layer of the sample along with a top plan view and side view of models that may be used for the top patterned layer for TE and TM incident light.
Figure 3B:
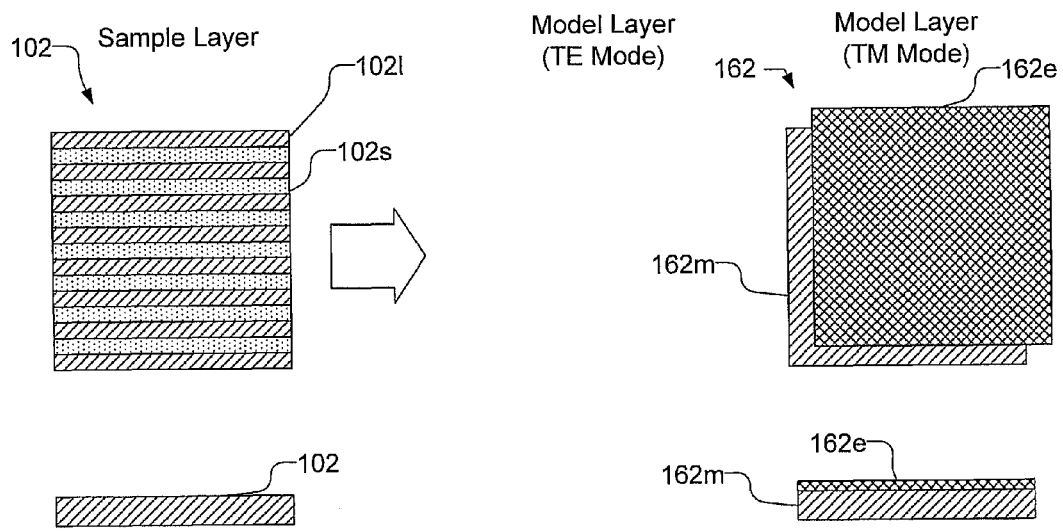
FIG. 3B illustrates a top plan view and a side view of an underlying patterned layer of the sample along with a top plan view and side view of a model that may be used for that underlying layer for TM incident light with respect to the top patterned layer.

FIG. 3A illustrates a top plan view and a side view of the top patterned layer 104 of the sample 100 along with a top plan view and side view of models 154 and 164 that may be used for the top patterned layer 104 when the incident light is in respective TE mode and TM mode with respect to the top patterned layer 104. FIG. 3B similarly illustrates a top plan view and a side view of the underlying patterned layer 102 of the sample 100 along with a top plan view and side view of a model that may be used for the underlying layer 102 when the incident light is in TM mode with respect to the top patterned layer 104. There is no need to model the underlying layer 102 when the incident light is in TE mode with respect to the top patterned layer 104.

As shown in FIG. 3A, when the incident light is TE polarized with respect to the top patterned layer 104, the top patterned layer 104 is modeled based on the effect that the periodic pattern has on the incident light, as opposed to a physical description of the structure. Thus, an "effective model" 154 is used for the top patterned layer 104. The effective model 154 includes two separate layers: an effective medium layer 154*e* and a conductive metal layer 154*m*, which are illustrated as being skewed in the top plan view of FIG. 3A so that both layers can be clearly seen. The effective medium layer 154*e* may have the combined optical properties of the transparent material 104*s* and the conductive material 104*l* of the sample 100. The ratio of the optical properties of the transparent material and the conductive material in the effective medium layer 154*e* may be a variable parameter in the model. The ratio of the optical properties of the transparent material and the conductive material in the effective medium layer 154*e* is related to the dimensional ratio of those materials in the measurement area of the sample 100, which may be used as an adequate seed value of that parameter. Additionally, the thickness of the effective medium layer 154*e* may be a variable parameter in the model. The thickness of the effective medium layer 154*e* is related to the depth of penetration of the light into the periodic pattern 104 in the sample 100, which is dependent on the size of the spaces 104*s* and the wavelengths of light used. By way of example, a thickness of approximately 20-40 nm for the effective medium layer 154*e* may be used as an adequate seed value for that parameter. The thickness of the underlying metal layer 154*m* should be sufficient that it is opaque to the incident light because the patterned layer 104 is opaque to TE incident light. Accordingly, as illustrated in FIG. 3B, layers of the sample 100 that underlie the patterned layer 104, e.g., patterned layer 102, need not be modeled when the incident light is in TE mode with respect to the top patterned layer 104. Using an effective model 154 for the top pattern layer 104 may be advantageous to simplify a measurement of an overlying film, such as film 109 shown in FIG. 1.

This effective model for TE mode can be further expanded to measure a non-periodic L/S structure because the physical structure of the sample is not directly included in the model. As long as the spaces between the conductive lines are small compared to the wavelength of the incident light, e.g., less than 50%, the non-periodic L/S structure is opaque to the TE polarized light and, therefore, can be modeled with the same effective media model.

When the incident light is TM polarized with respect to the top patterned layer 104, the light will convey additional information about the periodic pattern, such as the pitch, width, height, and sidewall angle of the lines. Thus, when TM polarized light is used; the model of top patterned layer 104 includes a physically descriptive model 164, as illustrated in FIG. 3A. The physically descriptive model 164 attempts to physically describe the top patterned layer 104. The TM polarized light will penetrate the top patterned layer 104 and will be incident on underlying layers, which must be modeled. Thus, the underlying patterned layer 102 is modeled when the incident light is TM polarized with respect to the top patterned layer 104. However, because the periodic pattern in the underlying layer 102 is orthogonally oriented with respect to the periodic pattern in the top layer 104, the incident light that is TM polarized with respect to the top patterned layer 104 is TE polarized with respect to the underlying patterned layer 102. Accordingly, an effective model 162 may be used to model the underlying patterned layer 102, as illustrated in FIG. 3B. Similar to the effective model 154 described in FIG. 3A, the effective model 162 for the underlying patterned layer 102 includes two separate layers: an effective medium layer 162e and an underlying conductive metal layer 162m, which are illustrated as skewed in the top plan view of FIG. 3B so that both layers can be seen.

Figure 4A:
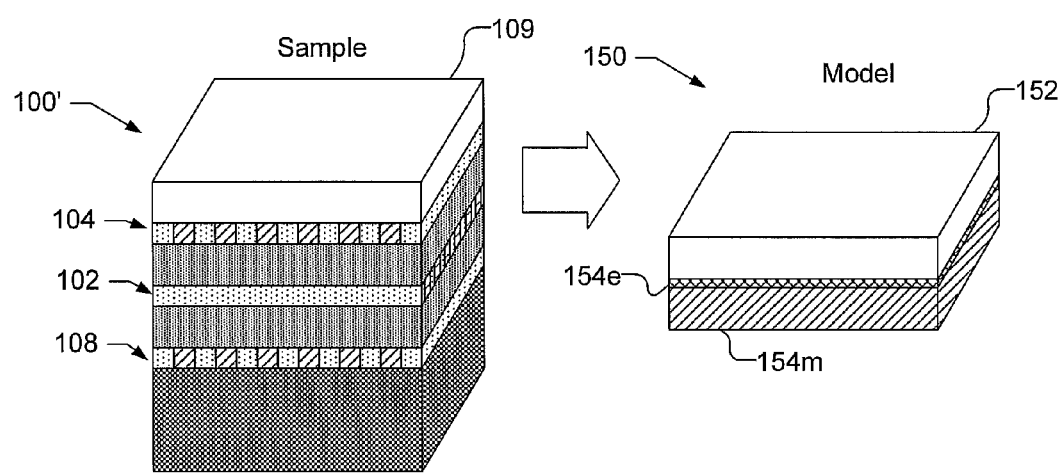
FIG. 4A illustrates perspective views of the sample from FIG. 1 and a model of the sample for TE polarized incident light with respect to the top patterned layer of the sample.

FIG. 4A illustrates perspective views of the sample 100 from FIG. 1, which is shown including layer 109, and a simplified model 150 of the sample 100. The simplified model 150 models the sample 100 when the incident light is TE polarized with respect to the top patterned layer 104 of the sample 100. As can be seen, the model 150 includes a portion 154 that is an effective model of the top patterned layer 104, which includes an effective medium layer 154e and a conductive metal layer 154m. Because the top patterned layer 104 of the sample prevents penetration of light to any underlying layers, there is no need to model the underlying patterned layers 102 or 108. The model 150, however, attempts to accurately describe the physical structure of the top layer 109 with model layer 152. Thus, the simplified model 150 can be used in the measurement of one or more layers over a patterned layer, without the need to accurately model the patterned layer.

Figure 4B:
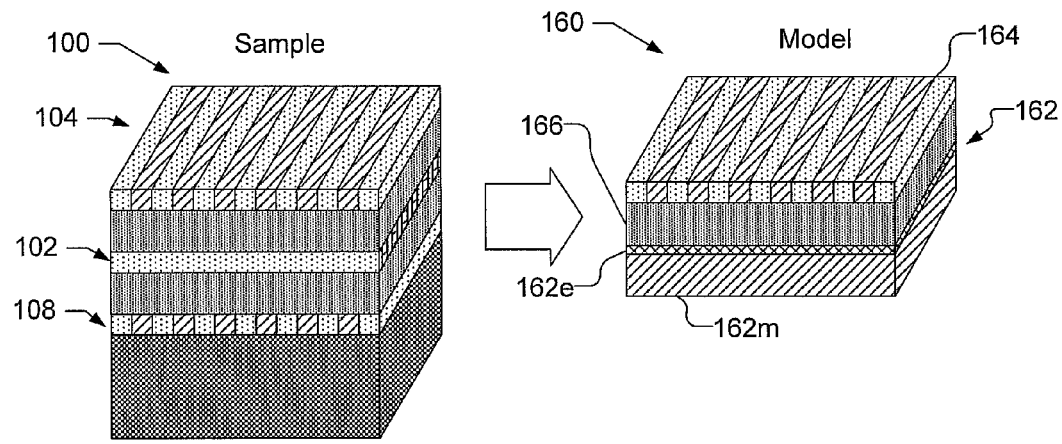
FIG. 4B illustrates perspective views of the sample from FIG. 1 and a model of the sample for TM polarized incident light with respect to the top patterned layer of the sample.

FIG. 4B illustrates another perspective view of the sample 100 (without the top layer 109) and a simplified model 160 of the sample 100. The simplified model 160 models the sample 100 when the incident light is TM polarized with respect to the top patterned layer 104 of the sample 100. As can be seen, the model 160 includes a portion 164 that attempts to accurately describe the physical structure of the periodic pattern on the top layer 104 of the sample 100 as well as a portion 166 that describes the structure of the underlying dielectric layer 106. The model 160 also includes a portion that is an effective model 162 of the underlying patterned layer 102 and includes an effective medium layer 162e and a conductive metal layer 162m. There is no reason to model layers of the sample 100 that are under the periodic layer 102, such as periodic layer 108, because the underlying layer 102 prevents the penetration of the light to these underlying layers.

Both TE and TM polarization may be used in a measurement, such as a measurement using combined TE and TM polarized light, measurement with unpolarized light, or measurement with other polarization, a single model may be used for both TE and TM polarizations. In this case, the model with more detailed physical structure among the TE and TM models can be used. For example, a model similar to that shown in FIG. 4B may be used, when the incident light uses both TE and TM polarization.

Figure 5A:
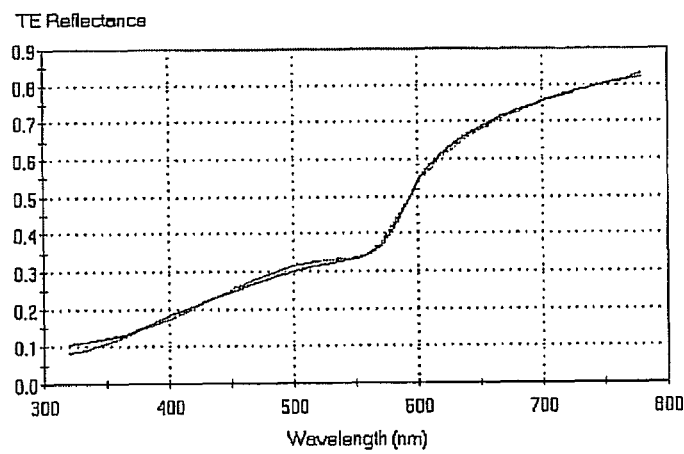
FIGS. 5A and 5B are TE reflectance and TM reflectance spectra, respectively, from a periodic line and space pattern.
Figure 5B:
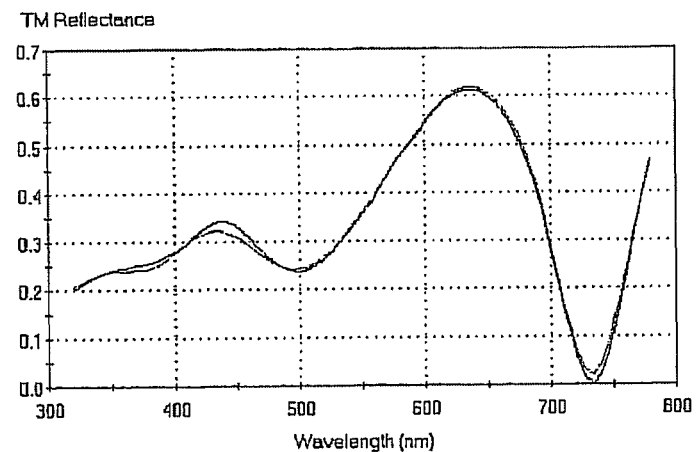
Figure 5C:
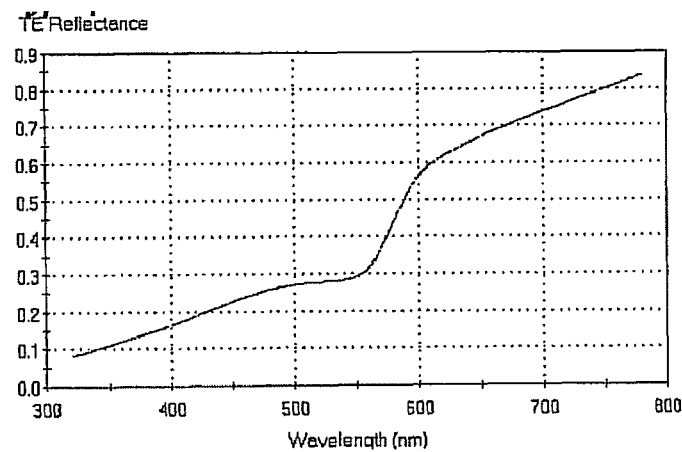
FIG. 5C is a TE reflectance spectrum from an effective model for a periodic line and space pattern.

FIGS. 5A and 5B are TE reflectance and TM reflectance spectra, respectively, from a periodic line and space pattern, similar to layer 104, with lines of copper and spaces of silicon dioxide, where the pitch is 200 nm and the width of the spaces is 100 nm. FIG. 5C is a TE reflectance spectrum from an effective model, similar to effective model 154 shown in FIG. 3A, with a 40 nm effective medium layer and an underlying uniform layer of copper (thickness≧100 nm). The effective medium layer has a combination of 80% of silicon dioxide and 20% of copper. As can be seen, the spectrum in FIG. 5C for the effective model is similar to the TE reflectance spectrum in FIG. 5A, illustrating the utility of the effective model. The TM reflectance spectra is FIG. 5B is different than the TE reflectance spectra in FIG. 5A because the TM reflectance spectra includes information about the physical structure of the measured periodic pattern.

Figure 6:
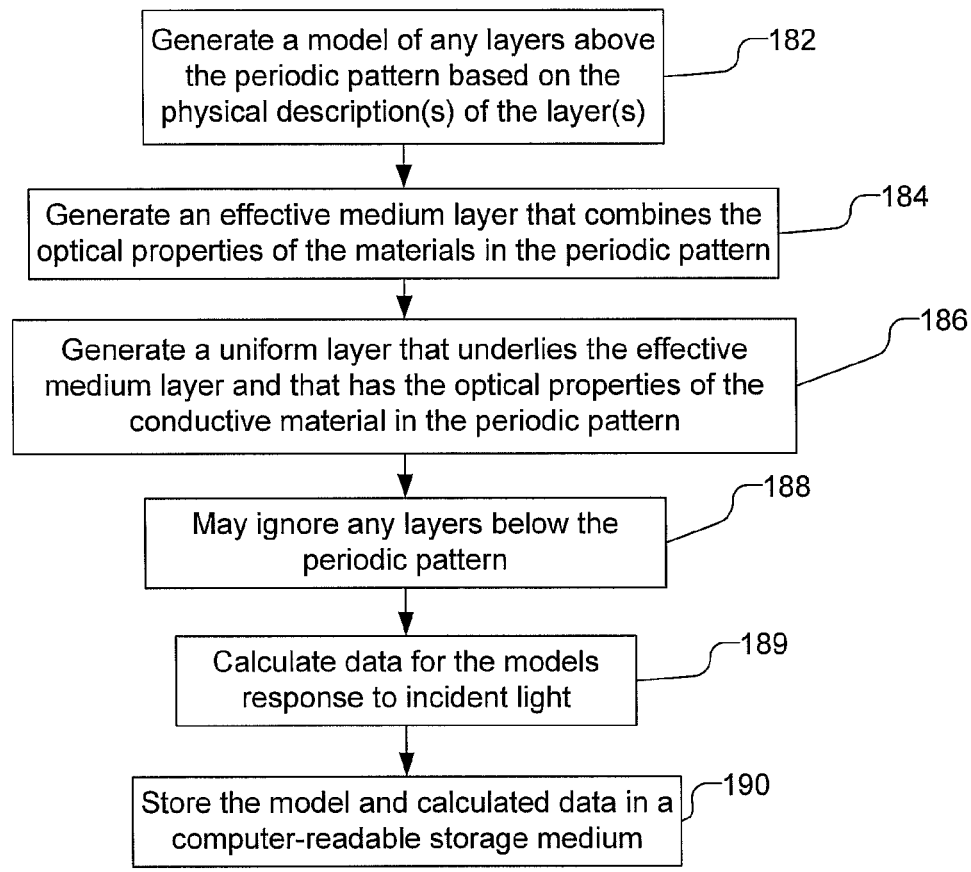
FIG. 6 illustrates a flow chart of the process of generating a model of a sample with a periodic pattern using an effective model for the periodic pattern.

FIG. 6 illustrates a flow chart of the process of generating a model of a sample with a periodic pattern using an effective model for the periodic pattern that is to be illuminated with TE polarized light. As discussed in FIG. 6, any layers above the periodic pattern are modeled based on the physical description of the layer (182). By way of example, if the layer above the periodic pattern is a uniform film (such as film 109 in FIG. 4A) or another cross-oriented periodic pattern (such as patterned layer 104 in FIG. 4B), the model attempts to accurately describe the physical structure of the layer. The periodic pattern that is to be illuminated with TE polarized light is modeled using an effective medium layer, which may be a uniform layer that combines the optical properties of the materials in the periodic pattern (184). Additionally, a uniform layer under the effective medium layer is generated, where the uniform layer has the optical properties of the conductive material in the periodic pattern (186).

Initial parameters of the effective model portion of the model, such as the materials and thicknesses may be selected based on known aspects of sample to be measured. For example, the materials of the lines 102l and spaces 102s of the bottom layer 102 in sample 100 in FIG. 1 are known. The optical property of the effective medium layer can be constructed by mixing the optical properties of the dielectric material and the conductive material together, e.g., in a ratio that is approximately the same as the ratio of those materials in the measurement area. Both the initial ratio and the initial thickness of the effective medium layer 162e (shown in FIG. 3B) may be based on knowledge of the structure being modeled, e.g., the percentage of dielectric material in an area equivalent to the measurement area of the measurement device. The thickness of the metal layer 162m (shown in FIG. 3B) is a non-variable parameter and is selected so that the layer is opaque to light.

As illustrated in FIG. 6, any layers of the sample that are below the periodic pattern may be ignored in the model as the periodic pattern is opaque to light.

Once the model is formed, data of the model's response to incident light (having the same parameters as the light used in the metrology tool) is acquired (189). In other words, data, such as the spectra from the model, is calculated. The data may be calculated using any desired technique, such as rigorous coupled wave analysis, or other known techniques, such as modal expansion and finite difference techniques. In general, the calculation of modeled spectra is well known and is described, e.g., in U.S. Pat. Nos. 5,963,329; 7,115,858; and U.S. Pat. No. 6,898,537, all of which are incorporated herein by reference. The model along with the calculated data for the model is then stored in a computer readable storage medium (190).

Figure 7:
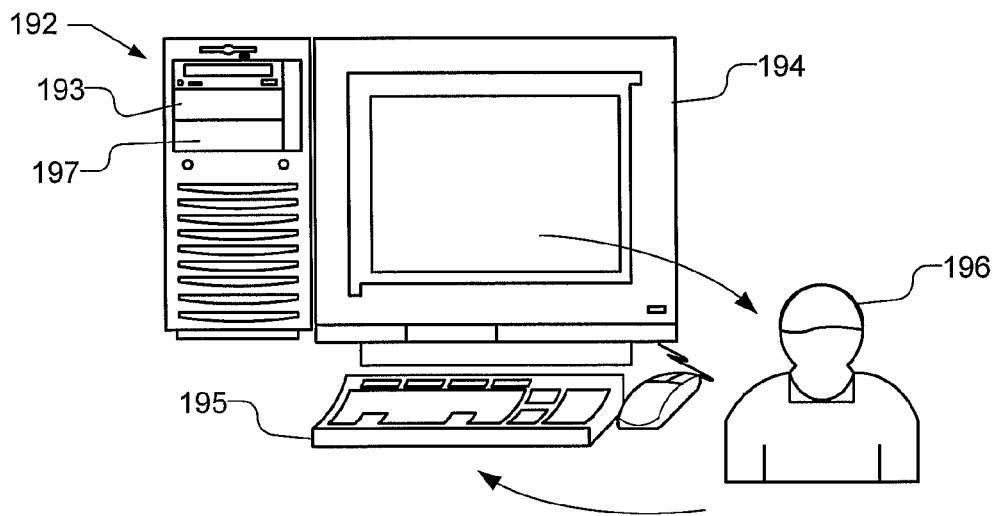
FIG. 7 illustrates a computer that includes a computer-readable storage medium that includes computer executable instructions adapted for generating a model using an effective model.

FIG. 7 illustrates a computer 192 that includes a computer-readable storage medium 193 that includes computer executable instructions adapted for generating a model using an effective model as described herein. Computer-readable storage medium 193 may be, e.g., hard disks, CD-ROMs, optical storage devices, flash memories, magnetic storage devices, tape, or any other appropriate medium. Generating computer instructions to perform the processes described herein is well within the abilities of those skilled in the art in light of the present disclosure. The computer 192 includes a user interface device 194, which may be a display or printer, as well as a user input device 195 that a user 196 may utilize to provide input during the generation of the model. The computer 192 also includes another computer-readable storage medium 197 that can be used to store the resulting model. In some embodiments, the computer 192 may be replaced by a bank of computers. In some embodiments, the computer 192 can be used to generate models in a real time analysis and in other embodiments, the computer 192 generates a plurality of models with different variable parameters prior to measurement of a sample sand stores the plurality of models in a library in an appropriate computer-readable storage medium. Additionally, one or both of the computer-readable storage mediums 193 and 197 may be separate from the computer 192, e.g., they may be linked through a network or the internet.

A sample with a periodic pattern may be measured using an effective model for the periodic pattern when the incident light is TE polarized with respect to the periodic pattern and using a metrology technique that is capable of measuring diffracting patterns. Examples of suitable metrology techniques are described in U.S. Pat. Nos. 5,963,329; 7,115,858 and U.S. Pat. No. 6,898,537, which are incorporated herein by reference.

Figure 8:
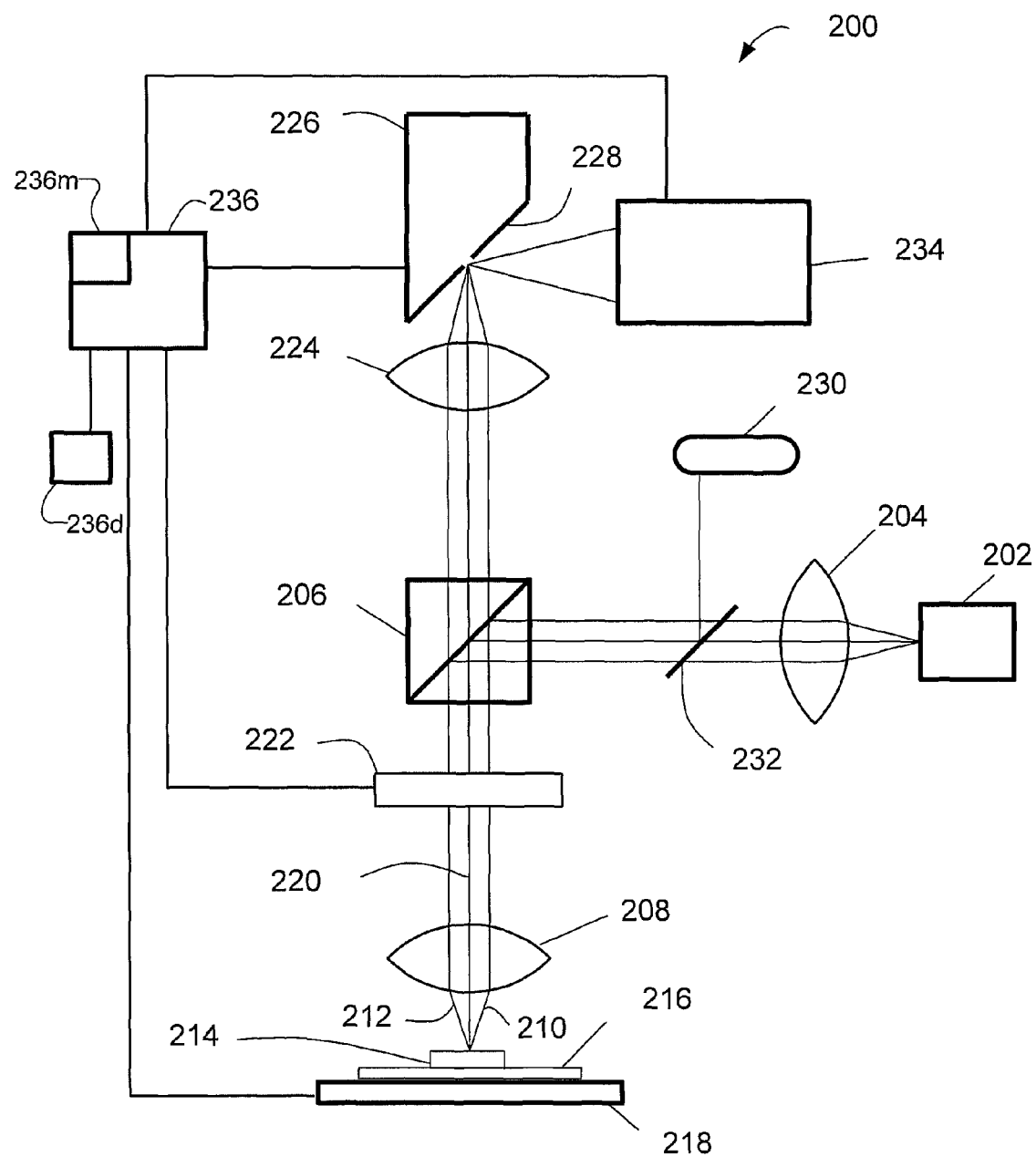
FIG. 8 illustrates a block diagram of a metrology tool that may be used to measure a sample using an effective model.

FIG. 8 illustrates a block diagram of a metrology tool 200 that may be used to measure a sample with a periodic pattern, such as that described in FIG. 1, using an effective model. Metrology tool 200 uses normal incidence light and includes a rotatable polarizer/analyzer 222 that, advantageously, aids in the measurement of diffracting structures.

Metrology tool 200 includes a broadband light source 202, such as an UV-visible light source with wavelengths, e.g., between 200 nm and 800 nm, that produces unpolarized light. The unpolarized light is collected and collimated by lens 204. Beam splitter 206 directs a portion of the collimated, broadband, unpolarized light beam toward the sample 214 that is held on a movable sample stage 218. The sample 214 may be similar to sample 100 shown in FIG. 1 and include one or more layers of periodic patterns that are orthogonally arranged.

Disposed between the beam splitter 206 and the sample 214 is the rotatable analyzer/polarizer ("RAP") 222. The light reflected by beam splitter 206 toward the sample passes through the RAP 222 and is linearly polarized. The rotation of RAP 222 is controlled by actuators (not shown) that are controlled by a computer 236 in a manner known to those skilled in the art. In another embodiment, RAP 222 is stationary while computer 236 rotates sample stage 218 so that the sample 214 is rotated relative to RAP 222.

The RAP 222 passes only the electric field component of the light that is coincident with the polarization axis of the RAP 222 and thus controls the polarization orientation of the light that is incident on the sample 214. During testing, the RAP 222 may be rotated to provide TM or TE polarization with respect to one of the periodic patterns on the sample 214. The RAP 222 may be, e.g., Glan Taylor air-spaced polarizer, a dichroic Polaroid sheet, or any other appropriate linearly polarizing device. The light from RAP 222 is focused by objective 208 so that the light is normally incident on sample 214. While marginal rays 210 and 212 are at small angles from the normal ray 220 on the sample, the angles are small enough to eliminate or greatly reduce any polarization effects that occur in conventional ellipsometers, and thus, the light is said to be normally incident on the sample 214. Because RAP 222 is rotated relative to the sample 214, i.e., RAP 222 and/or sample 214 is rotated, the polarization orientation of the incident light need not be aligned with the underlying structure in the sample 214 prior to the metrology process. Consequently, metrology tool 200 may be used, advantageously, with a wafer stage 218 that is capable of any or all of x, y, z, and/or θ movement, as well as a stage that is capable of r-θ movement only.

Light that is reflected or diffracted from the sample 214 is re-collimated by lens 208 and passes through the RAP 222, which linearly polarizes the light. Any light that is diffracted from sample 214 will have different electric field component intensities and phase from the light that is incident on the structure 214. The RAP 222 passes only the electric field component of the reflected beam that is coincident with the polarization axis of the RAP 222. Thus, RAP 222 advantageously permits detection of different spectral components of the diffracted light.

The light then passes through the beam splitter 206. The light is then focused by lens 224 to the entrance slit of a spectrometer 226. In another embodiment, lens 208 may be replaced with a microscope objective and lens 224 removed. Spectrometer 226 may be a conventional CCD, PDA, or similar type spectrometer that disperses the full spectrum of the polarized light into spectral components across an array of detector pixels. Each pixel corresponds to a different wavelength, and thus the spectrometer 226 generates a spectral signal as a function of wavelength $\lambda$ that is transmitted to computer 236. The spectral signal is corrected for electronic background noise as is well known in the art.

The sample 210 may be viewed and aligned using, e.g., a lamp 230 that produces visible light to provide flood illumination via movable mirror 232. This flood illumination is reflected off mirror 228 to a camera and pattern recognition system 234, which may be coupled to computer 236. The pattern recognition system 234 can provide a measure of orientation of sample 214 relative to the RAP 222, if desired, as well as serve as a conventional detector for the sample height. The pattern recognition system 234 provides data to the computer 236, which accordingly adjusts the height of stage 218.

Of course, if desired other metrology systems, such as scatterometers, reflectometers or other normal incidence devices, may be used.

The computer 236 may be similar to computer 192 shown in FIG. 6 and include a computer-readable storage medium 236m that includes computer executable instructions adapted for generating a model using an effective model as described herein, for a real time generation of the models. Alternatively, the computer 236 may include a computer-readable storage medium 236m that includes a plurality of models in a library.

Figure 9:
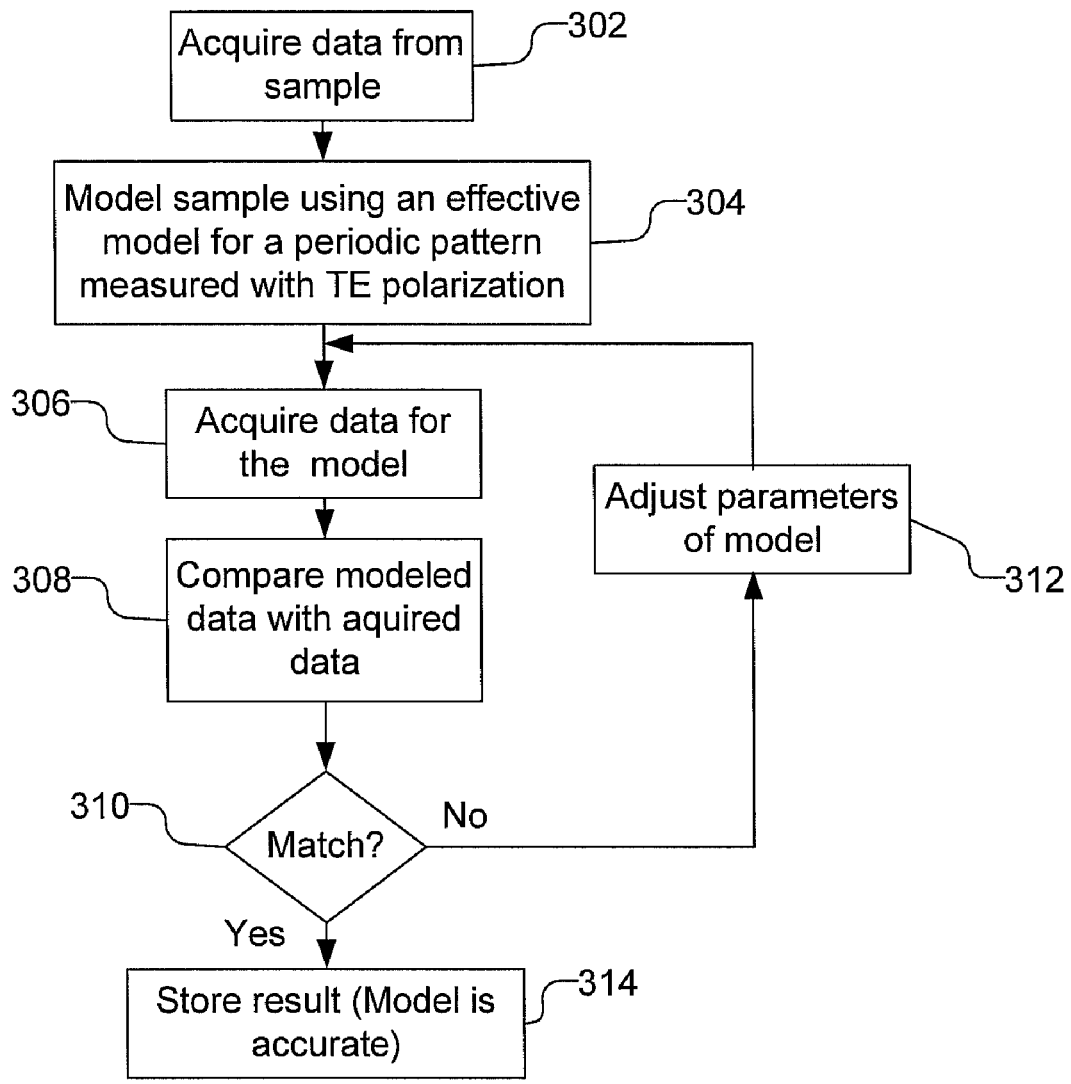
FIG. 9 is a flow chart illustrating a method of measuring a sample that includes overlying periodic patterns that are orthogonally arranged.

FIG. 9 is a flow chart 300 illustrating a method of measuring a sample that includes a periodic pattern using an effective model. Data from the sample is acquired using at least TE polarized light with respect to a periodic pattern, e.g., the periodic pattern on the bottom layer 102 of the sample 100, using metrology device 200 described above (302). The data may be, e.g., spectral information and/or scattering information, but for the sake of simplicity, the present disclosure will refer to acquiring and using spectral information. Thus, by way of example, the metrology tool 200 produces polarized light that is incident on the sample. The light that is scattered and/or reflected from the sample is detected and data is acquired from the detected light. The acquired data is indicative of the characteristics of the sample, such as the CD, depth, and sidewall profile of the periodic pattern on the top layer 104.

A model of the sample is generated using an effective model for the periodic pattern that is measured with TE polarized light with respect to that periodic pattern (304). The model may be generated on the fly or multiple models with different parameters may be pre-generated and stored in a library. It should be understood that the initial parameters of the model of the sample may not be accurate. For example, the parameters, e.g., the materials and dimensions, of the first portion of the model may be based on the desired structure of the top layer 104 of the sample 100.

Once the initial model is formed, data of the model's response to incident light (having the same parameters as the light used in the metrology tool) is acquired (306). In other words, data, such as the spectra from the model, is calculated, which may be done in real time or pre-generated and stored in the library and acquired by the computer 236 from the library.

The modeled data is then compared to the acquired data (308). By way of example, the Mean-Squared Error (MSE) may be used to compare the acquired and modeled data. If the modeled data is considered to match the measured data (310), the portion of the model of the sample that physically describes the sample may be assumed to be accurate (314) and the result is stored, e.g., in a computer memory or storage, and/or displayed to the user. Of course, the portion of the model that is an effective model is known to be physically inaccurate, but may provide some information, such as the percentage of dielectric material that is present in the measurement area.

If, however, the modeled data and the measured data do not match (310), the values of the variable parameters in the model are adjusted (312). Thus, in a real-time analysis, the variable parameters may be adjusted using the Levenberg-Marquardt algorithm, and the data is recalculated using the new optical model (306). By way of example, the thickness (or other variable parameters) of the sample is adjusted. With the use of a library, the parameters of the model are adjusted by selecting model in the library with different parameters from the previous model and the data for the new model is acquired (306).

The modeled data from the new model is then again compared to the acquired data (308). If the acquired and modeled data still do not match, the values of the variable parameters of the model are again adjusted (312). In this manner, the parameters of the model are iteratively adjusted until the modeled data for the model and the acquired data from the sample closely match. A match between the data can be determined when further adjustment of the optical model does not improve the fit or when the fit, which may be determined from the MSE, is below a preselected threshold. When the modeled data and measured data are considered to match, the portion of the model of the sample that physically describes the sample may be assumed to be accurate (314). The results may then be stored in a computer-readable storage medium 236*m* or reported to a user interface device 236*d*, such as a display or printer of the computer 236 (FIG. 8). In general, fitting the calculated data from a model to the acquired data from the sample is well known and is described, e.g., in U.S. Pat. Nos. 5,963,329; 7,115,858; and U.S. Pat. No. 6,898,537, all of which are incorporated herein by reference.

Measurements performed at a plurality of locations of a sample can be compared to obtain relative measurements for the different locations. The ability to resolve differences in a sample is important to control the many processes, such as chemical mechanical polishing.

There is a possibility that more than one set of parameters for the model will produce calculated data that matches the acquired data. Thus, a verification procedure may be used to ensure that the measurements made using an effective model are correct. In one embodiment, the measurement may be verified by measuring a plurality of locations on the substrate and using the relation between the measurements as verification of the accuracy of the measurements. For more discussion of verification and for use of an effective model for a film with an underlying complicated periodic pattern, see U.S. Ser. No. 10/859,330, entitled "Modeling a Sample with an Underlying Complicated Structure" by William A. McGahan, filed on Jun. 1, 2004, which has the same assignee as the present disclosure and the entirety of which is incorporated by reference.

Figure 10:
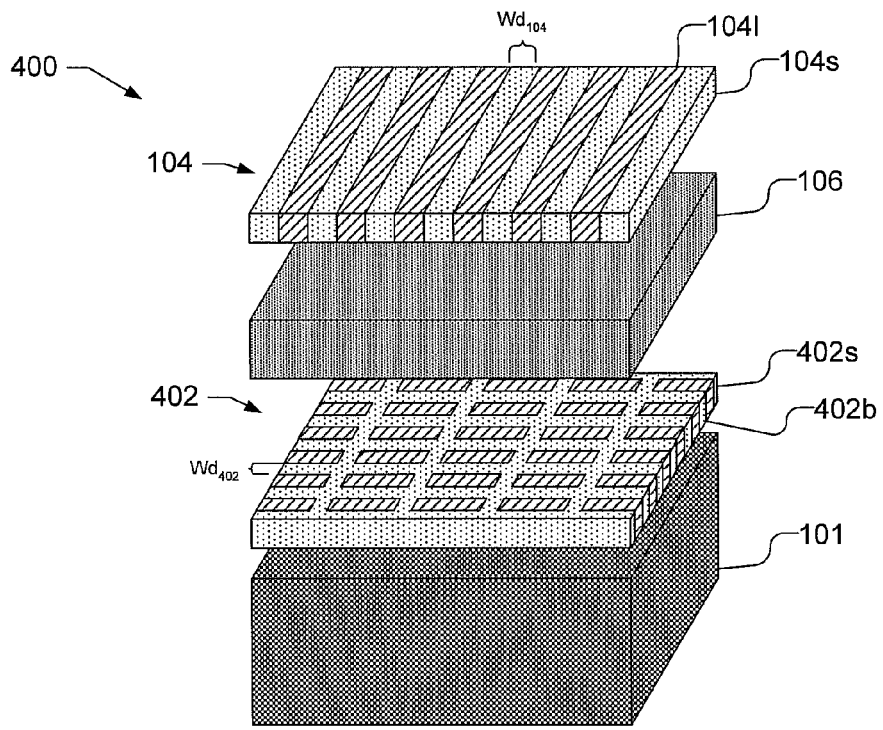
FIG. 10 illustrates an exploded perspective view of a sample that includes overlying periodic patterns, in which the bottom periodic pattern is periodic in two dimensions.

An effective model may be used for a portion of a sample that includes a pattern that is periodic in two dimensions, as opposed to one dimension as illustrated in FIG. 1. FIG. 10 illustrates an exploded perspective view of a sample 400 that is similar to sample 100 shown in FIG. 1, except that the underlying layer 402 has a two dimensional periodic pattern of features 402*b* and spaces 402*s*. The features 402*b* may be contacts, vias, spots or other similar structures that are made from a conductive material, such as a metal or metal alloy, and the surrounding spaces 402*s* are made from at least partially transparent material, such as a dielectric.

Figure 11A:
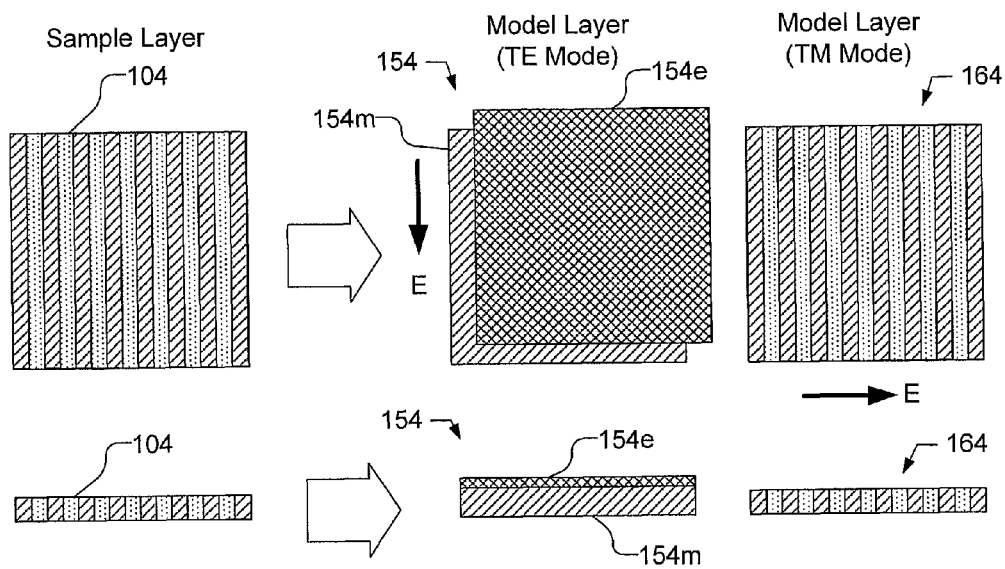
FIG. 11A illustrates a top plan view and a side view of the top patterned layer of the sample along with a top plan view and side view of models that may be used for the top patterned layer for TE and TM incident light with respect to the top patterned layer.

FIG. 11A illustrates a top plan view and a side view of the top layer 104 of the sample 400 along with a top plan view and side view of models 154 and 164 that may be used for the top patterned layer 104 when the incident light is in respective TE mode and TM mode with respect to the top patterned layer 104. FIG. 11A is similar to FIG. 3A which illustrates the modeling of the top patterned layer of the sample 100.

Figure 11B:
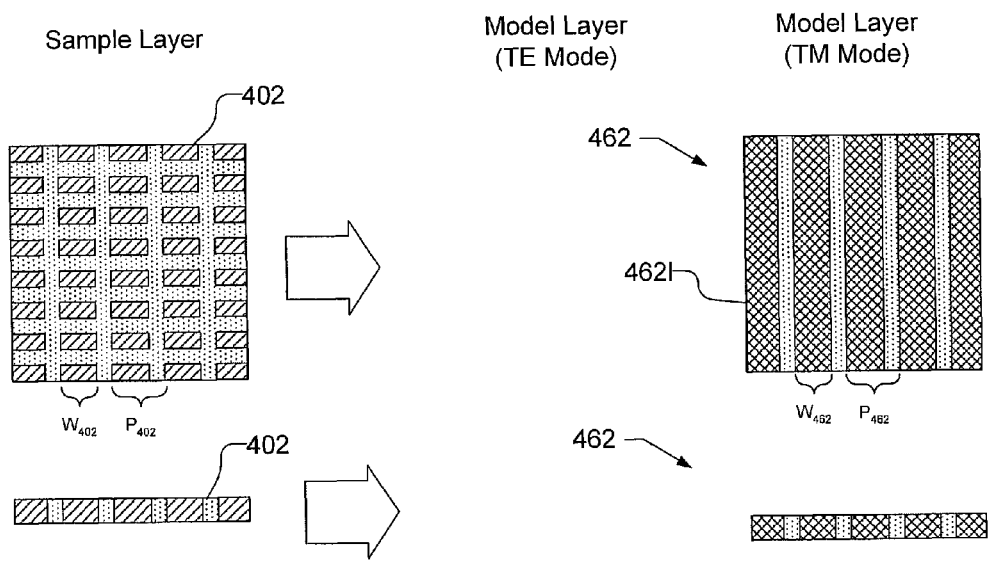
FIG. 11B illustrates a top plan view and a side view of the underlying patterned layer of the sample that is periodic in two dimensions along with a top plan view and side view of models that may be used for TM incident light with respect to the top patterned layer.

FIG. 11B illustrates a top plan view and a side view of the underlying patterned layer 402 of the sample 400 along with a top plan view and side view of a model that may be used for the underlying patterned layer 402 when the incident light is in TM mode with respect to the top patterned layer 104. There is no need to model the underlying layer 402 when the incident light is in TE mode with respect to the top patterned layer 104.

As shown in FIGS. 11A and 11B, when the incident light has TE polarization with respect to the top layer 104, the top layer 104 is modeled based on the "effect" that the structure has on the incident light, as opposed to an accurate description of the physical structure. The metal layer 154*m* in the effective model 154 is opaque to light and, accordingly, the model does not need to include any of the underlying layers, such as the layer 402. Thus, as illustrated in FIG. 11B, the underlying layer 402 is not modeled when the light is in TE mode with respect to the top layer 104.

When the incident light has TM polarization with respect to the top layer 104, the top layer 104 is modeled with a physically descriptive model 164. An effective model 462 is used to model the underlying patterned layer 402. However, because the periodic pattern in layer 402 of the sample is periodic in two dimensions, layer 402 will not be completely opaque to the incident light. Accordingly, the effective model 462 for layer 402 physically describes the periodic pattern in one dimension, i.e., the dimension that is perpendicular to the electric field component of the light. In other words, the periodic pattern in layer 402 of the sample has a periodicity in two dimensions, but the effective model simplifies the layer to a one dimensional periodicity. There are multiple ways to construct the simplified model based on the physical property of the 2D structure. In one method, the line width $W_{462}$ and pitch $P_{462}$ of the periodic pattern in the effective model 462 is the same as the feature width $W_{402}$ and pitch $P_{402}$ of the periodic pattern in the layer 402 along the dimension that is perpendicular to the electric field component of the light, e.g., along the horizontal axis shown in FIG. 11B. The optical properties of the lines 462l, however, are a combination of the materials in the periodic pattern in layer 402, e.g., in approximately the same ratio as the materials in layer 402 along the same direction. In another method, the pitch $P_{462}$ of the periodic pattern and the optical properties of the lines 462l is the same as the feature pitch $P_{402}$ and optical properties of the patter 402b. The line width $W_{462}$ is adjusted to reflect the periodic nature along the other direction in the physical structure. Because the effective model 462 is not completely opaque to the incident light, it is necessary to also model any layers that underlie layer 402.

Figure 12:
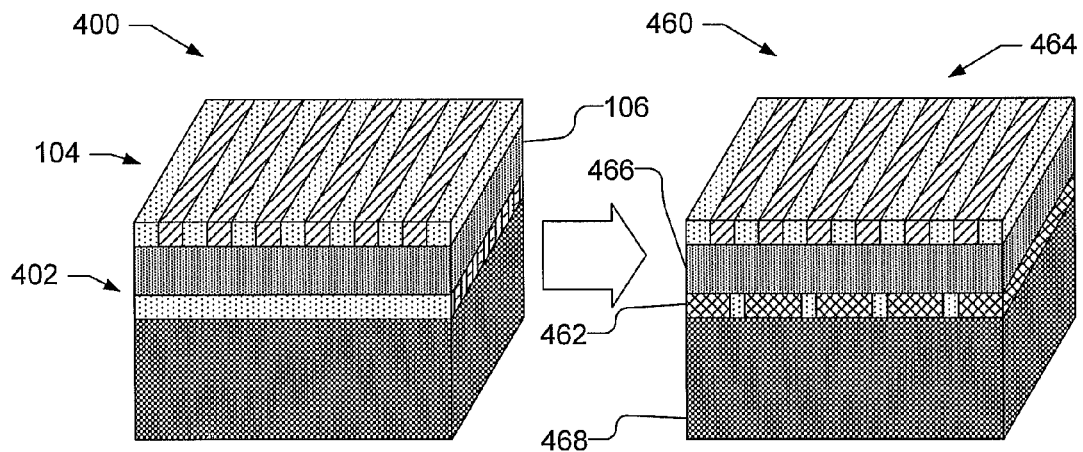
FIG. 12 illustrates perspective views of the sample from FIG. 10 and a simplified model of the sample.

FIG. 12 illustrates perspective views of the sample 400 from FIG. 10 and a simplified model 460 of the sample 400. The simplified model 460 models the sample 400 when the incident light is TM polarized with respect to the top patterned layer 104 of the sample 400. As can be seen, the model 460 includes a portion 464 that attempts to accurately describe the physical structure of the periodic pattern on the top layer 104 of the sample 400 as well as a portion 466 that describes the structure of the underlying dielectric layer 106. The model 460 also includes a portion that is an effective model 462 of the bi-periodic patterned layer 402. The layer 101 under layer 402 is modeled as layer 468 because the layer 402 is not completely opaque to light.

FIG. 13 illustrates an exploded perspective view of another sample 500 with a two dimensional periodic pattern, similar to that shown in FIG. 10, except the two dimensional periodic pattern 502 is above another periodic pattern 504. As with sample 400, the features 502b may be contacts, vias, spots or other similar structures that are made from a conductive material, such as a metal or metal alloy, and the surrounding spaces 502s are made from at least partially transparent material, such as a dielectric.

Figure 14A:
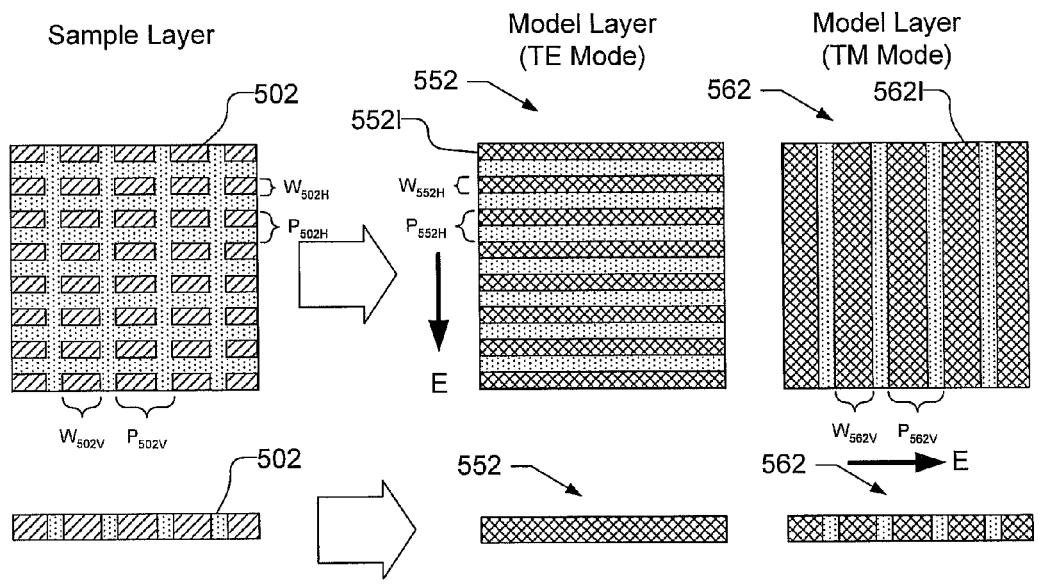
FIG. 14A illustrates a top plan view and a side view of the top periodic layer of the sample from FIG. 13 along with a top plan view and side view of models that may be used for the top patterned layer when the incident light is in TE mode and the TM mode with respect to the top patterned layer.

FIG. 14A illustrates a top plan view and a side view of the top periodic layer 502 of the sample 500 along with a top plan view and side view of models 552 and 562 that may be used for the top patterned layer 502 when the incident light is in respective TE mode and TM mode with respect to the vertical direction (in the figure) of the top patterned layer 502. FIG. 14A is similar to FIG. 3A which illustrates the modeling of the top patterned layer of the sample 100.

Figure 14B:
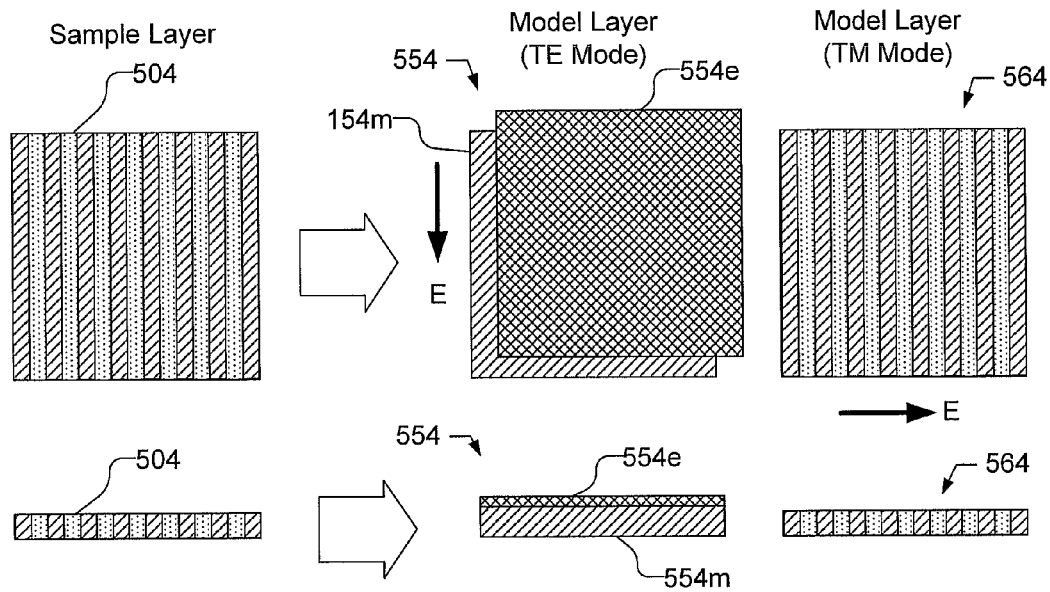
FIG. 14B illustrates a top plan view and a side view of the underlying patterned layer of the sample from FIG. 13 along with a top plan view and side view of models that may be used for the underlying patterned layer when the incident light is in TE mode and the TM mode with respect to the top patterned layer.

FIG. 14B illustrates a top plan view and a side view of the underlying patterned layer 504 of the sample 500 along with a top plan view and side view of models 554 and 564 that may be used for the underlying patterned layer 502 when the incident light is in respective TE mode and the TM mode with respect to the vertical direction (in the figure) of the top patterned layer 502.

As shown in FIGS. 14A, when the incident light has TE polarization with respect to the vertical direction (in the figure) of the top patterned layer 502, an effective model 552 is used for the top patterned layer 502. The effective model 552 is based on the "effect" that the structure has on the incident light, as opposed to an accurate description of the physical structure. However, because the periodic pattern in top patterned layer 502 of the sample 500 is periodic in two dimensions, the top patterned layer 502 will not be completely opaque to the incident light. Accordingly, the effective model 552 for layer 502 physically describes the periodic pattern in one dimension, i.e., the dimension that is parallel to the electric field component of the light. In other words, the periodic pattern in layer 502 of the sample has a periodicity in two dimensions, but the effective model simplifies the layer to have a periodicity with one less dimension. The line width $W_{552H}$ and pitch $P_{552H}$ of the periodic pattern in the effective model 552 is the same as the feature width $W_{502H}$ and pitch $P_{502H}$ of the periodic pattern in the patterned layer 502 along the dimension that is parallel to the electric field component of the light, e.g., along the vertical axis shown in FIG. 14A. The optical properties of the lines 552l, however, are a combination of the materials in the periodic pattern in layer 502, e.g., in approximately the same ratio as the materials in layer 502 along the same direction. Because the effective model 552 is not completely opaque to the incident light, it is necessary to also model any layers that underlie layer 502.

Thus, as illustrated in FIG. 14B, the bottom periodic layer 504 is modeled. Because the incident light is TE polarized with respect to the bottom periodic layer 504, the bottom periodic layer 104 is modeled with an effective model 554, similar to layer 104, shown in FIG. 3A. The effective model 554 includes an effective medium layer 554e and an underlying metal layer 554m.

When the incident light has TM polarization with respect to the vertical direction (in the figure) of the top patterned layer 502, a different effective model 562 is used for the top patterned layer 502, as illustrated in FIG. 14A. The effective model 562 is similar to the effective model 462 described in FIG. 11B. Thus, the line width $W_{562V}$ and pitch $P_{562V}$ of the periodic pattern in the effective model 562 is the same as the feature width $W_{502V}$ and pitch $P_{502V}$ of the periodic pattern in the patterned layer 502 along the dimension that is parallel to the electric field component of the light, e.g., along the horizontal axis shown in FIG. 14A. The optical properties of the lines 562l are a combination of the materials in the periodic pattern in layer 502, e.g., in approximately the same ratio as the materials in layer 502 along the same direction. Because the effective model 562 is not completely opaque to the incident light, it is necessary to also model any layers that underlie layer 502.

Thus, as illustrated in FIG. 14B, the bottom periodic layer 504 is modeled. However, because the incident light is TM polarized with respect to the periodic pattern in the bottom periodic layer 504, the bottom periodic layer 504 is modeled with a physically descriptive model 564. Again, because the bottom periodic layer 504 is not completely opaque to the incident light, it is necessary to also model any layers that underlie layer 504.

FIG. 15 illustrates a perspective view of a model 550 for the sample 500 from FIG. 13 when incident light is TE polarized with respect to the vertical direction (in the figure) of the top periodic layer 502 (as illustrated by models 552 and 554 in FIGS. 14A and 14B). As illustrated in FIG. 15, the simplified model 550 includes an effective model portion 552 for the top periodic layer 502 of the sample 500, which reduces the periodic pattern from two dimensions to a single dimension. Underlying layers including layer 506 and 504 are also modeled, as modeled layer 556 and effective model 554. The bottom patterned layer 504 of the sample can be modeled as an effective model 554, which includes a uniform effective medium layer 554e and a uniform metal layer 554m, which is opaque to light. Consequently, any layers (including periodic patterns, films, or the substrate) below the bottom patterned layer 504 need not be modeled.

FIG. 16 illustrates a perspective view of a model 560 for the sample 500 from FIG. 13 when incident light is TM polarized with respect to the vertical direction (in the figure) of the top periodic layer 502 (as illustrated by models 562 and 564 in FIGS. 14A and 14B). As illustrated in FIG. 16, the simplified model 560 includes an effective model portion 562 for the top periodic layer 502 of the sample 500, which reduces the periodic pattern from two dimensions to a single dimension. Underlying layers including layer 506 and 504 are also modeled, as modeled layer 566 and model layer 564. The bottom patterned layer 504 of the sample is modeled with a portion 564 that based on the physical description of the layer 504, as opposed to using an effective model, because the light is TM polarized with respect to the periodic pattern in layer 504. As light will pass through the bottom periodic layer 504 in the sample, underlying layers (including periodic patterns, films, or the substrate) below the bottom patterned layer 504 are also modeled, as illustrated by layers 568 in FIG. 16.

Although the present disclosure is illustrated in connection with specific embodiments for instructional purposes, the present invention is not limited thereto. Various adaptations and modifications may be made without departing from the scope of the invention. For example, while the use of light having a normal angle of incidence is described, non-normal angles of incidence may also be used. Therefore, the spirit and scope of the appended claims should not be limited to the foregoing description.

What is claimed is:

1. A method comprising:
producing a model of a sample, the sample having a pattern on a layer, the pattern comprising a conductive material and an at least partially transparent material, producing a model of the sample comprises:
modeling the pattern based on the effect that the pattern has on incident light that is TE polarized with respect to the pattern, wherein modeling the pattern comprises:
generating a first uniform film that combines the optical properties of the conductive material and the at least partially transparent material of the pattern based on a ratio of materials in the pattern on the layer; and
generating a second uniform film of the conductive material of the pattern, the second uniform film underlying the first uniform film;
wherein producing a model of the sample further comprises storing the model of the sample in a computer-readable storage medium.

2. The method of claim 1, wherein the pattern is a periodic pattern.

3. The method of claim 2, wherein the periodic pattern includes series of conductive lines and at least partially transparent spaces, the conductive lines comprise metal and the at least partially transparent spaces comprise a dielectric.

4. The method of claim 1, wherein the pattern is non-periodic.

5. The method of claim 1, wherein the at least partially transparent material of the pattern has a width that is less than 50% of a wavelength of the incident light.

6. The method of claim 1, wherein the sample further comprises a second layer that overlies the pattern and producing a model of the sample further comprises modeling the second layer based on the physical characteristics of the second layer.

7. The method of claim 1, wherein the pattern on the layer is a first pattern on a first layer, the sample further comprising a second pattern on a second layer that overlies the first pattern, wherein the first pattern has a periodicity in a first direction and the second periodic pattern has a periodicity in a second direction that is orthogonal to the first direction, wherein producing a model of the sample further comprises modeling the second pattern based on the physical characteristics of the second pattern.

8. The method of claim 1, wherein the sample further comprises a second pattern that underlies the pattern, wherein producing a model of the sample further comprises not modeling the second pattern.

9. The method of claim 1, further comprising determining a characteristic of the sample at a location that includes the pattern, wherein determining the characteristic comprises:
producing light that is incident on the sample, the light is TE polarized with respect to the pattern;
detecting light after the light that is incident on the sample interacts with the sample; and
acquiring data from the detected light, the acquired data being indicative of the characteristic of the sample at a location that includes the pattern on the layer;
calculating data for the model of the sample;
comparing the acquired data and the calculated data to determine the characteristic of the sample; and
storing the characteristic of the sample in a computer-readable storage medium.

10. The method of claim 9, wherein the acquired data and the calculated data is spectral data.

11. The method of claim 9, further comprising iteratively adjusting at least one parameter of the model of the sample, recalculating data for the model of the sample, and comparing the acquired data from the sample with the recalculated data for the model of the sample until an acceptable fit between the acquired data and the calculated data occurs.

12. The method of claim 9, wherein producing a model and calculating data for the model is performed prior to acquiring data from the sample.

13. The method of claim 9, wherein calculating data for the model of the sample comprises performing rigorous coupled-wave analysis.

14. A non-transitory computer readable storage medium comprising computer executable instructions adapted to perform a method comprising:
producing a model of a sample, the sample having a pattern on a layer, the pattern comprising a conductive material and an at least partially transparent material, producing a model of the sample comprises:
modeling the pattern based on the effect that the pattern has on incident light that is TE polarized with respect to the pattern, wherein modeling the pattern comprises:
generating a first uniform film that combines the optical properties of the conductive material and the at least partially transparent material of the pattern based on a ratio of materials in the pattern on the layer; and
generating a second uniform film of the conductive material of the pattern, the second uniform film underlying the first uniform film;
wherein producing a model of the sample further comprises storing the model of the sample.

15. The computer readable storage medium of claim 14, wherein the sample further comprises a second layer that overlies the pattern and wherein the method further comprises modeling the second layer based on the physical characteristics of the second layer.

16. The computer readable storage medium of claim 14, wherein the pattern on the layer is a first pattern on a first layer, the sample further comprising a second pattern on a second layer that overlies the first pattern, wherein the first pattern has a periodicity in a first direction and the second pattern has a periodicity in a second direction that is orthogonal to the first direction, and wherein the method further comprises modeling the second pattern based on the physical characteristics of the second pattern.

17. The computer readable storage medium of claim 14, wherein the pattern is a periodic pattern.

18. The computer readable storage medium of claim 17, wherein the periodic pattern includes series of conductive lines and at least partially transparent spaces, the conductive lines comprise metal and the at least partially transparent spaces comprise a dielectric.

19. The computer readable storage medium of claim 14, wherein the pattern is non-periodic and the at least partially transparent material of the pattern has a width that is less than 50% of a wavelength of the incident light.

20. A method comprising:
modeling a sample, the sample comprising at least a first periodic pattern on a first layer and a second periodic pattern on a second layer, the second periodic pattern underlying the first periodic pattern, wherein the first periodic pattern and the second periodic pattern includes conductive material and at least partially transparent material, and wherein the first periodic pattern has a periodicity in a first direction and the second periodic pattern has a periodicity in a second direction that is orthogonal to the first direction, modeling the sample comprising:
generating a first portion of the model for the first layer that is based on the physical characteristics of the first periodic pattern; and
generating a second portion of the model for the second layer based on the affect of the second periodic pattern on incident light that is TE polarized with respect to the second periodic pattern, the second portion of the model including a first uniform film that combines the optical properties of the conductive material and the at least partially transparent material of the second periodic pattern based on a ratio of materials in the pattern on the layer, and a second uniform film of the conductive material of the second periodic pattern;
storing the model of the sample in a computer-readable storage medium.

21. The method of claim 20, wherein each of the first periodic pattern and the second periodic pattern include a series of conductive lines and at least partially transparent spaces, the conductive lines comprise metal and the at least partially transparent spaces comprise a dielectric.

22. The method of claim 20, wherein the at least partially transparent spaces have a width that is less than 50% of a wavelength of the incident light.

23. The method of claim 20, wherein the sample further comprises a third periodic pattern that underlies the second pattern, wherein producing a model of the sample further comprises not modeling the third periodic pattern.

24. The method of claim 20, the method further comprising producing multiple models of the sample, each of the multiple models of the sample having at least one different parameter; and storing the multiple models of the sample in the computer-readable storage medium.

25. A method comprising:
producing a model of a sample, the sample comprising a layer with a periodic pattern that includes a conductive material and an at least partially transparent material, the periodic pattern is a two-dimensional periodic pattern having a first periodicity in a first direction and a second periodicity in a second direction that is orthogonal to the first direction, producing a model of the sample comprises:
modeling the periodic pattern based on the effect that the periodic pattern has on incident light that is TE polarized with respect to the first periodicity in the first direction, wherein modeling the periodic pattern comprises:
generating a model periodic pattern that is based on the physical characteristics of the periodic pattern only along the first direction;
wherein the sample further comprises a second periodic pattern on a second layer that underlies the periodic pattern, the second periodic pattern comprising a conductive material and an at least partially transparent material, the second periodic pattern has a periodicity only in the second direction, wherein producing a model of the sample further comprises:
modeling the second periodic pattern based on the effect that the second periodic pattern has on incident light that is TE polarized with respect to the second periodic pattern, wherein modeling the second periodic pattern comprises:
generating a first uniform film that combines the optical properties of the conductive material and the at least partially transparent material of the second periodic pattern based on a ratio of materials in the pattern on the layer;
generating a second uniform film of the conductive material of the second periodic pattern, the second uniform film underlying the first uniform film; and
storing the model of the sample in a computer-readable storage medium.

26. The method of claim 25, wherein the periodic pattern includes series of conductive features and at least partially transparent spaces, the conductive features comprise metal and the at least partially transparent spaces comprise a dielectric.

27. The method of claim 26, wherein the spaces have a width that is less than 50% of a wavelength of the incident light along the second direction.

28. The method of claim 25, wherein the sample further comprises a third layer that overlies the periodic pattern and producing a model of the sample further comprises modeling the third layer based on the physical characteristics of the third layer.

29. The method of claim 25, wherein the periodic pattern on the layer is a first periodic pattern on a first layer, the sample further comprising a third periodic pattern on a third layer that overlies the first periodic pattern, wherein producing a model of the sample further comprises modeling the third periodic pattern based on the physical characteristics of the third periodic pattern along the first direction.

30. A non-transitory computer readable storage medium comprising computer executable instructions adapted to perform a method comprising:
producing a model of a sample, the sample comprising a layer with a periodic pattern that includes a conductive material and an at least partially transparent material, the periodic pattern is a two-dimensional periodic pattern having a first periodicity in a first direction and a second periodicity in a second direction that is orthogonal to the first direction, producing a model of the sample comprises:
modeling the periodic pattern based on the effect that the periodic pattern has on incident light that is TE polarized with respect to the first periodicity in the first direction, wherein modeling the periodic pattern comprises:
generating a model periodic pattern that is based on the physical characteristics of the periodic pattern only along the first direction;

wherein the sample further comprises a second periodic pattern on a second layer that underlies the periodic pattern, the second periodic pattern comprising a conductive material and an at least partially transparent material, the second periodic pattern has a periodicity only in the second direction, and wherein the method further comprises:

modeling the second periodic pattern based on the effect that the second periodic pattern has on incident light that is TE polarized with respect to the second periodic pattern, wherein modeling the second periodic pattern comprises:

generating a first uniform film that combines the optical properties of the conductive material and the at least partially transparent material of the second periodic pattern based on a ratio of materials in the pattern on the layer; and generating a second uniform film of the conductive material of the second periodic pattern, the second uniform film underlying the first uniform film; and storing the model of the sample.

31. The computer readable storage medium of claim 30, wherein the sample further comprises a third layer that overlies the periodic pattern and wherein the method further comprises modeling the third layer based on the physical characteristics of the third layer.

32. The computer readable storage medium of claim 30, wherein the periodic pattern on the layer is a first periodic pattern on a first layer, the sample further comprising a third periodic pattern on a third layer that overlies the first periodic pattern, and wherein the method further comprises modeling the third periodic pattern based on the physical characteristics of the third periodic pattern along the first direction.

* * * * *